(12) United States Patent  
Lloyd et al.

(10) Patent No.: US 8,870,833 B2
(45) Date of Patent: Oct. 28, 2014

(54) ANTI-ROTATION AND REMOVAL RESISTANT ADAPTER FOR USE WITH A SYRINGE

(75) Inventors: Ronald Lloyd, Deland, FL (US); Eric M. Sampson, Deland, FL (US)

(73) Assignee: Covidien LP, Mansfield, MA (US)

( * ) Notice: Subject to any disclaimer, the term of this patent is extended or adjusted under 35 U.S.C. 154(b) by 1287 days.

(21) Appl. No.: 12/333,371

(22) Filed: Dec. 12, 2008

(65) Prior Publication Data

US 2009/0163859 A1 Jun. 25, 2009

Related U.S. Application Data

(60) Provisional application No. 61/008,784, filed on Dec. 21, 2007.

(51) Int. Cl.
  *A61M 5/31* (2006.01)
  *A61M 5/34* (2006.01)
  *A61M 5/32* (2006.01)
(52) U.S. Cl.
  CPC ............. *A61M 5/347* (2013.01); *A61M 5/3293* (2013.01)
  USPC ....................................................... 604/240

(58) Field of Classification Search
  USPC .......................... 604/240–243, 533–535, 539
  See application file for complete search history.

(56) References Cited

U.S. PATENT DOCUMENTS

| | | |
|---|---|---|
| 5,224,939 A | 7/1993 | Holman et al. |
| 5,591,143 A | 1/1997 | Trombley, III et al. |
| 5,609,584 A | 3/1997 | Gettig et al. |
| 5,830,195 A | 11/1998 | Peters et al. |

*Primary Examiner* — Manuel Mendez
(74) *Attorney, Agent, or Firm* — Lisa E. Winsor, Esq.

(57) ABSTRACT

An adapter and syringe assembly is described in this application which includes a syringe and an adapter for anti-rotation, removal resistant connection to the syringe. The syringe has a body defining a fluid reservoir, a plunger assembly including a plunger head dimensioned to be slidably received within the reservoir, a fluid outlet, and a first coupling member. The adapter has a body portion defining a fluid channel, a collar portion, and a second coupling member configured to engage the first coupling member to secure the adapter to the syringe. The syringe includes at least one rib and a surface of the collar includes at least one protrusion. The at least one rib and the at least one protrusion are configured and positioned to interact to facilitate attachment of the adapter to the syringe but to resist detachment of the oral dose tip adapter from the syringe. The body portion of the adapter may define an oral dose tip or a needle hub assembly.

25 Claims, 6 Drawing Sheets

ANTI-ROTATION AND REMOVAL RESISTANT ADAPTER FOR USE WITH A SYRINGE

CROSS-REFERENCE TO RELATED APPLICATION

The present application claims the benefit of and priority to U.S. Provisional Patent Application Ser. No. 61/008,784 filed Dec. 21, 2007, which is incorporated herein by reference in its entirety.

BACKGROUND

1. Technical Field

The present disclosure generally relates to removal resistant adapters and, more particularly, to removal resistant adapters for connecting an oral dose tip or a needle hub assembly to a syringe.

2. Description of the Related Art

Syringes are well known in the medical arts and typically include a body defining a fluid reservoir and a plunger movably positioned within the reservoir. A needle cannula may be fixedly supported on a distal end of the body. Alternatively, the distal end of the body may include a connector, e.g., a luer, for securing the syringe to an intravenous (IV) catheter assembly or a needle hub assembly. Such syringes are commonly used to inject medication or the like directly into a patient's body or into an IV line.

Oral dose syringes are also known in the art and typically include a body defining a fluid reservoir and a plunger which is movably positioned within the reservoir. The distal end of the body includes an extension defining a channel having a diameter substantially larger than the diameter of a needle cannula. The extension defines a smooth exterior surface and is insertable into the mouth of a patient to orally introduce medication or the like into a patient.

Although oral dose syringes are effective in performing the desired function, a medical office or hospital must stock both luer tip syringes and oral dose syringes in order to perform both of these desired procedures.

Accordingly, it would be desirable to provide an adapter having an oral dose tip which could be secured to a luer tip syringe to obviate the need for stocking oral dose syringes. It would also be desirable to provide an adapter for securing an oral dose tip or a needle hub assembly to a syringe which is resistant to detachment from the syringe after the tip or hub assembly has been secured to the syringe.

SUMMARY

An adapter and syringe assembly is described in this application which includes a syringe and an adapter. The syringe has a body defining a fluid reservoir, a plunger assembly including a plunger head dimensioned to be slidably received within the reservoir, a fluid outlet, and a first coupling member. The adapter has a body portion defining a fluid channel, a collar portion, and a second coupling member configured to engage the first coupling member to secure the adapter to the syringe. The body portion of the adapter may be configured as an oral dose tip, or in the alternative, as a needle hub assembly. The syringe includes at least one rib and a surface of the collar includes at least one protrusion. The at least one rib and the at least one protrusion are configured and positioned to interact to facilitate attachment of the adapter to the syringe but to resist detachment of the adapter from the syringe.

In one embodiment, the first coupling member and the second coupling member are configured to be rotatably coupled. The first and second coupling members may be luer-type connectors.

The first coupling member may be substantially annular. In one embodiment, the at least one rib is formed on an external surface of the first coupling member and the at least one protrusion is formed on an inner surface of the collar portion in a position to engage the at least one rib to resist rotatable detachment of the adapter from the syringe. The at least one protrusion may include a plurality of protrusions and the at least one rib may include a plurality of ribs. In one embodiment, the plurality of ribs are spaced about the first coupling member and the plurality of protrusions are positioned about the inner surface of the collar portion.

The collar portion may be substantially elliptical and include a pair of sidewalls, a top wall and a bottom wall. The plurality of protrusions may be positioned on the inner surface of the pair of sidewalls of the collar portion. One or more protrusions may also be formed on the top and bottom walls.

In one embodiment, the top and bottom walls of the collar portion define a concavity and a first tab extends from within the cavity of the top wall of the collar portion and a second tab extends from within the concavity of the bottom wall of the collar portion, such that when the first and second tabs are compressed towards each other, the protrusions on the top and bottom walls engage the ribs on the first coupling member. The first and second tabs may extend outwardly of a periphery of the collar portion.

In one embodiment, the collar portion is connected to the body portion by at least one spring member. The at least one spring member may include a pair of spaced spring members which convert the collar portion to the body portion.

In one embodiment, the body portion, the collar portion and the second coupling member are integrally formed.

BRIEF DESCRIPTION OF THE DRAWINGS

The foregoing and other features and advantages of the present disclosure will be more fully understood from the following detailed description of the embodiments, taken in conjunction with the accompanying drawings, in which.

DETAILED DESCRIPTION OF THE EMBODIMENTS

Figure 1:
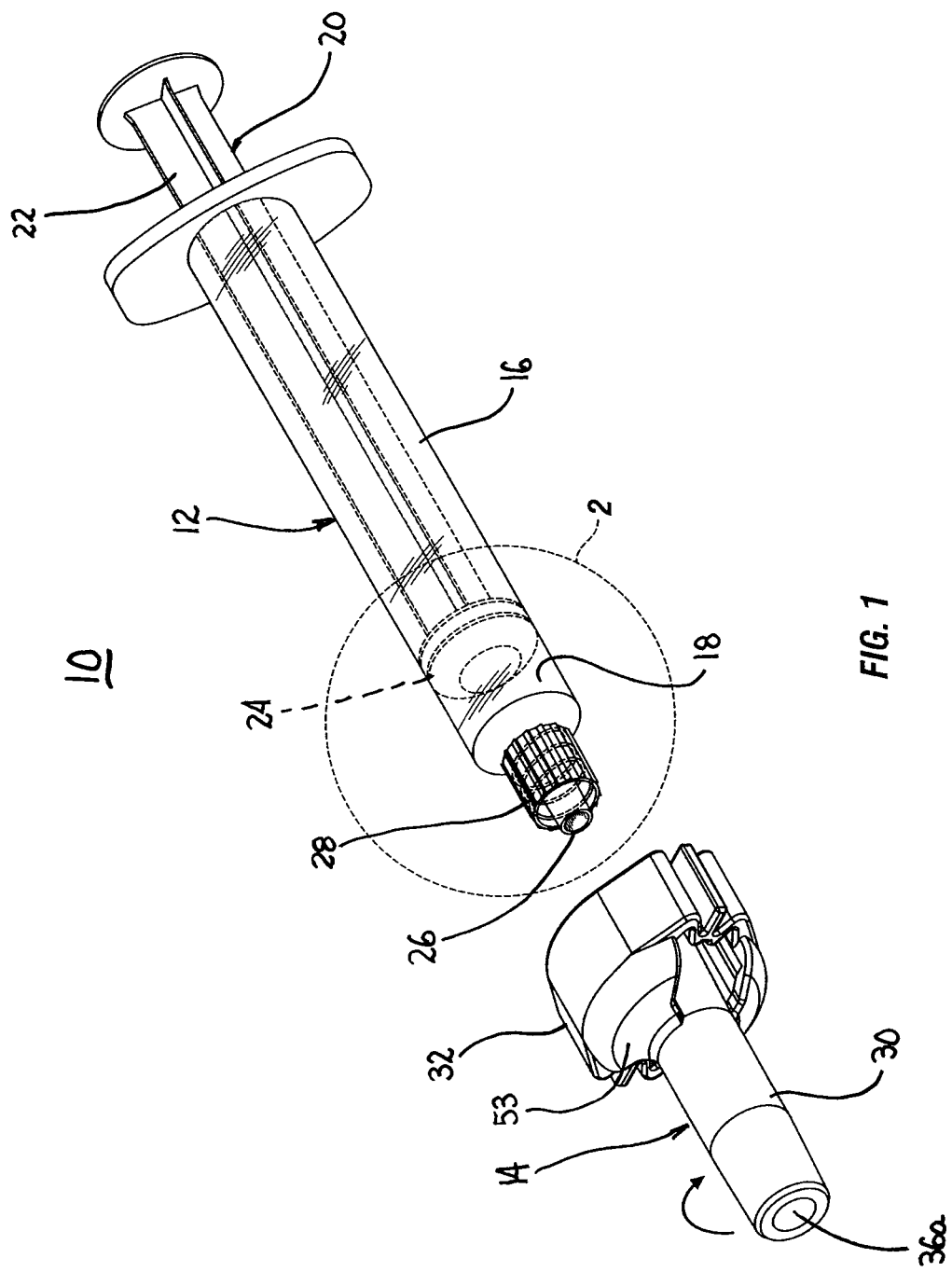
FIG. 1 is an exploded perspective view of a syringe and anti-rotation, removal resistant oral dose tip adapter in accordance with the principles of the present disclosure.

Embodiments of the presently disclosed anti-rotation, removal resistant adapter and syringe assembly will now be described in detail with reference to the drawings wherein like reference numerals designate identical or corresponding elements in each of the several views.

Figure 2:
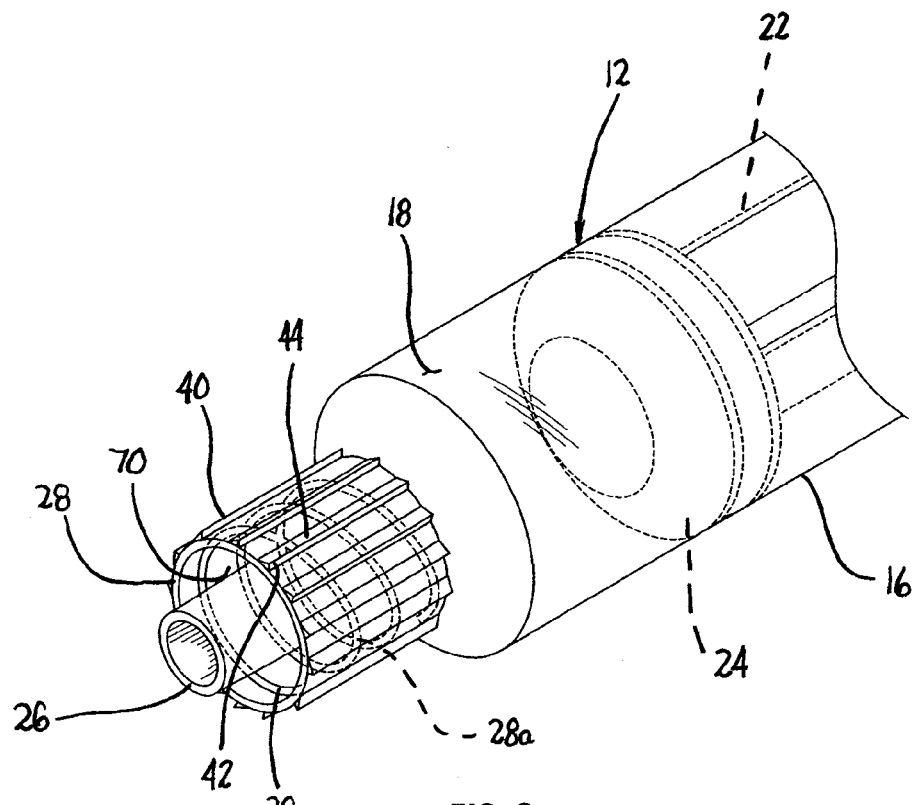
FIG. 2 is an enlarged view of the area of interest of FIG. 1 in accordance with the principles of the present disclosure.

Referring to FIGS. 1 and 2, the presently disclosed anti-rotation and removal resistant adapter and syringe assembly for orally dispensing a medicinal fluid is shown generally as 10. Adapter and syringe assembly 10 includes a syringe 12 and an oral dose tip adapter 14. Syringe 12 includes a body 16 defining a fluid reservoir 18 and a plunger assembly 20. Plunger assembly 20 includes a plunger rod 22 and a plunger head 24. Plunger head 24 is dimensioned to be slidably received within reservoir 18 of body 16 to deliver fluid from reservoir 18 to a fluid outlet 26 which is supported on a distal end of body 16 in fluid communication with reservoir 18. Syringe 12 also includes an annular coupling member 28 positioned partially about fluid outlet 26 as will be discussed in further detail below.

Figure 3:
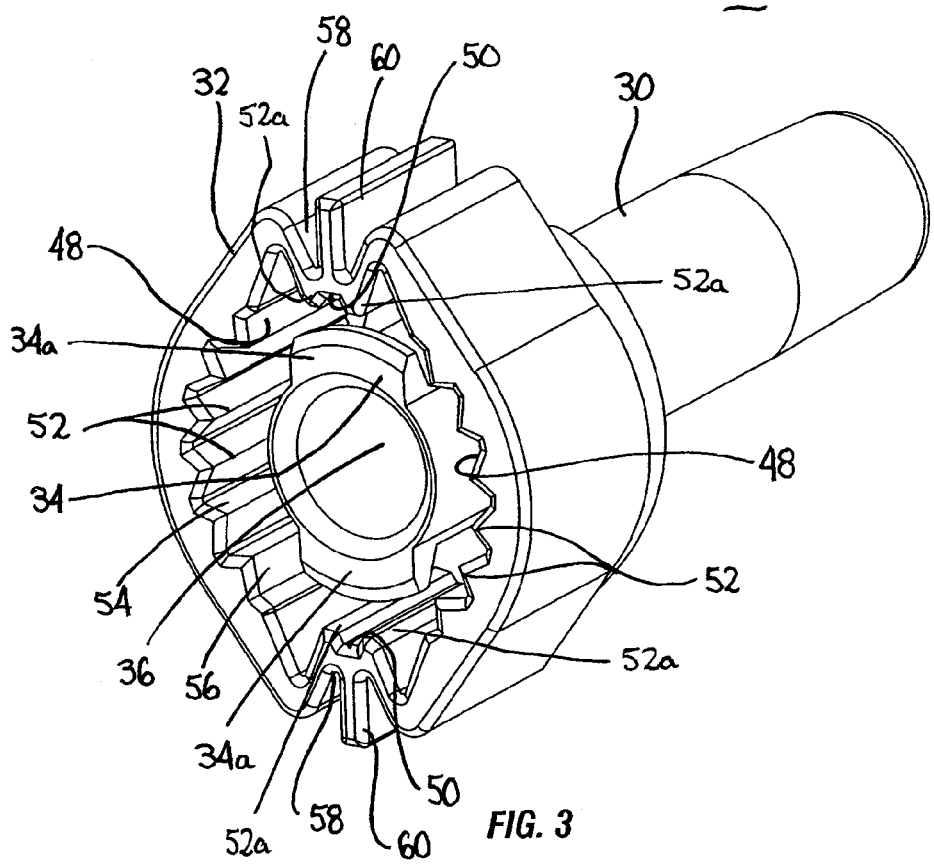
FIG. 3 is a rear perspective view of the oral dose tip adapter shown in FIG. 1 in accordance with the principles of the present disclosure.
Figure 4:
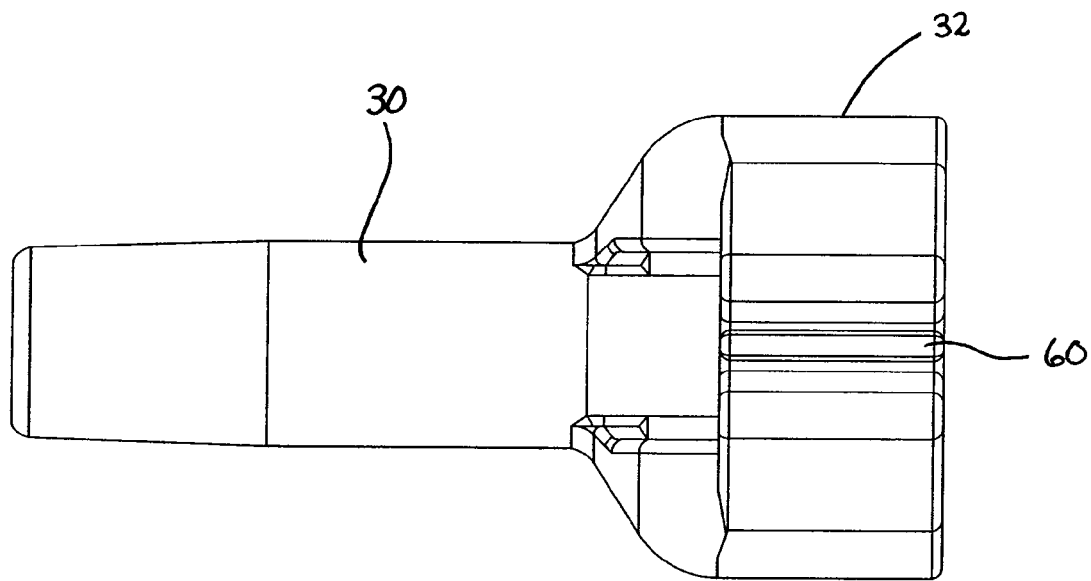
FIG. 4 is a top view of the oral dose tip adapter shown in FIG. 3.
Figure 5:
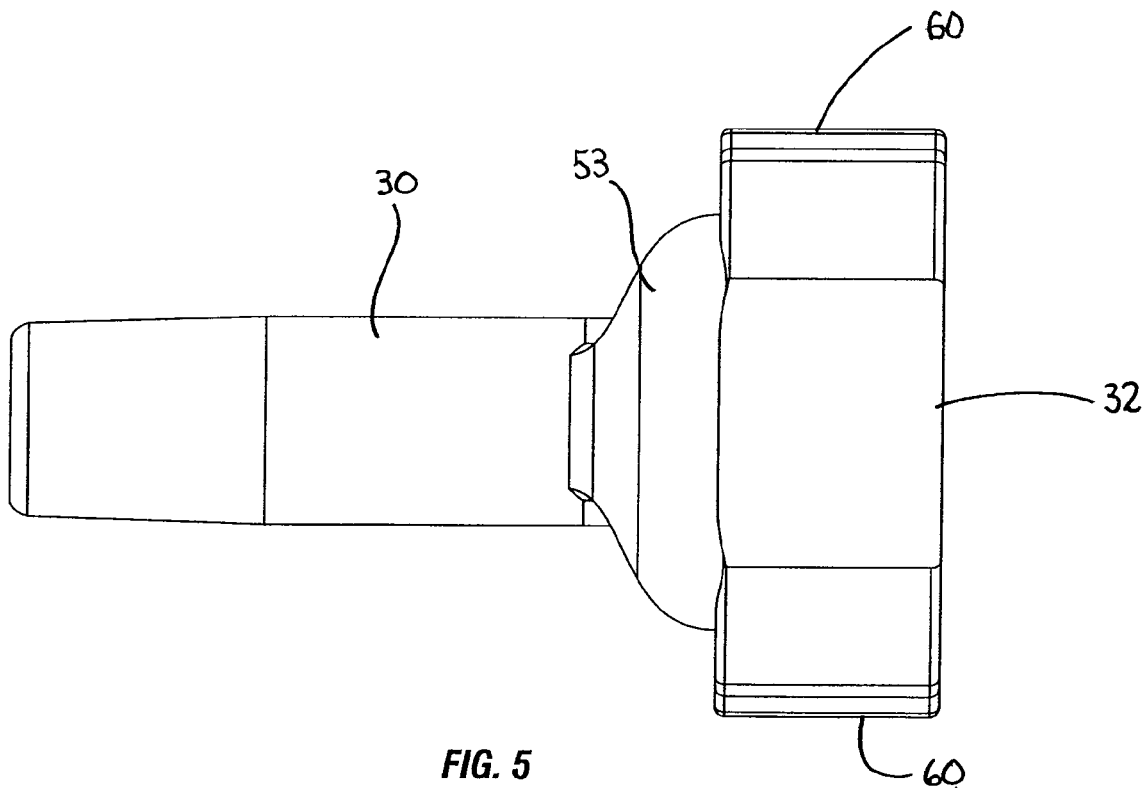
FIG. 5 is a side view of the oral dose tip adapter shown in FIG. 3.
Figure 6:
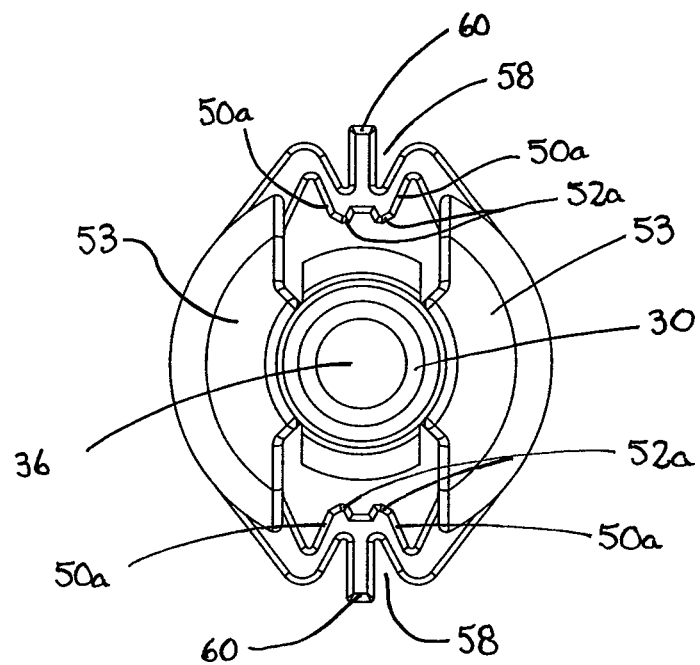
FIG. 6 is a front view of the oral dose tip adapter shown in FIG. 3.
Figure 7:
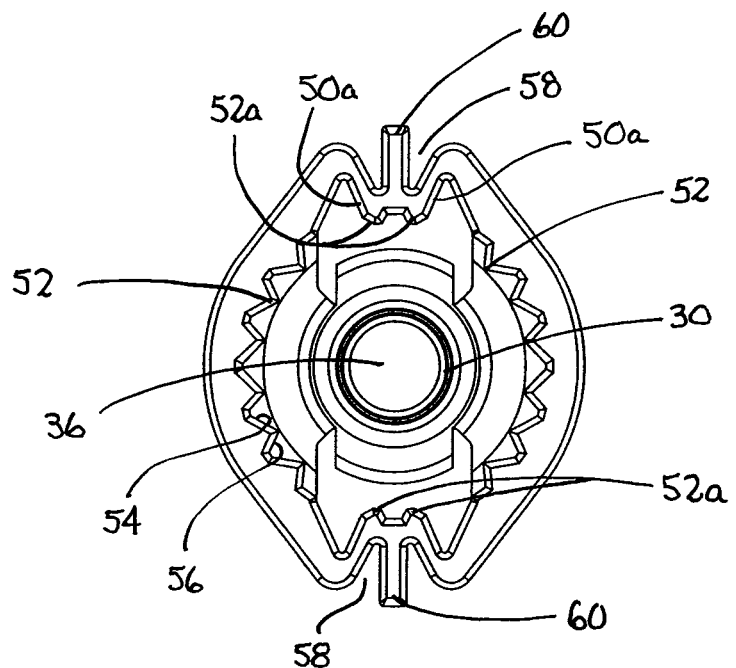
FIG. 7 is a rear view of the oral dose tip adapter shown in FIG. 3.
Figure 8:
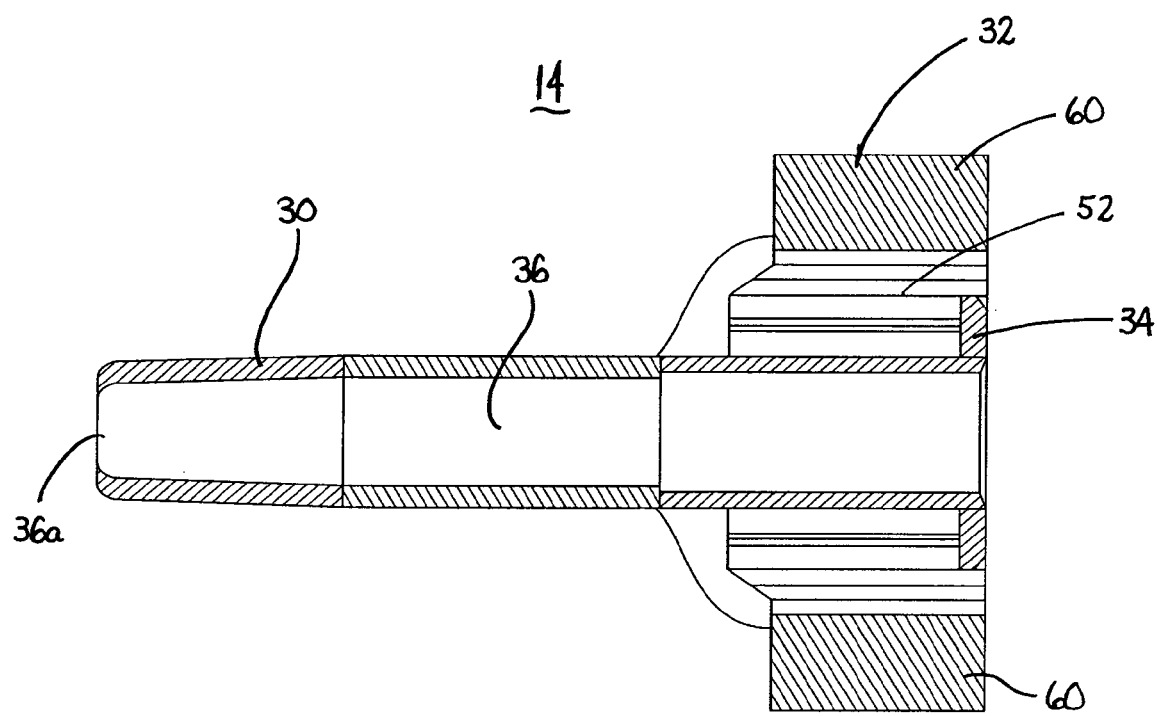
FIG. 8 is a side cross-sectional view of the oral dose tip adapter shown in FIG. 1.

Referring also to FIGS. 3-8, oral dose tip adapter 14 is formed from a metal or plastic material, e.g., polyethylene, and includes a body portion 30, a collar portion 32, and a coupling member 34 (FIG. 3). Body portion 30 is elongated and defines a fluid channel 36 (FIG. 8) having an outlet 36a. Collar portion 32 is integrally attached to a proximal end of body portion 30 and will be described in further detail below. Coupling member 34 is configured to releasably engage annular coupling member 28 of syringe 12 to releasably secure oral dose tip adapter 14 to syringe 12. As illustrated, coupling member 34 (FIG. 3) may be a male luer-type coupling member which includes tabs 34a configured to rotatably engage threads 28a of annular coupling member 28 (FIG. 2) which is configured as a male luer-type coupling member. It is envisioned that a variety of different types of coupling members and luer-type connectors known in the art could be used to couple oral dose tip adapter 14 to syringe 12.

Referring to FIGS. 1 and 2, annular coupling member 28 has an external surface which includes one or more longitudinal, spaced ribs 40. As illustrated, a plurality of longitudinal, spaced ribs are provided on coupling member 28. Each rib 40 has a substantially right triangularly-shaped cross-section having a substantially vertical sidewall 42 and a sloped sidewall 44. Sloped side wall 42 defines an angle of between about 15° and about 75° and can be about 30°, wherein "X" is an interior angle defined between sloped sidewall 44 and a base wall of the triangle formed by sloped sidewall 44, substantially vertical sidewall 42 and the base wall.

Referring to FIGS. 1 and 3, collar portion 32 of oral dose tip adapter 14 is positioned about coupling member 34 and is substantially oval or elliptical in configuration. Collar portion 32 has an inner wall surface having sidewalls 48 and top and bottom walls 50 as illustrated in FIG. 3. Each of sidewalls 48 includes a series of teeth 52. Top and bottom walls 50 also include teeth 52a. Each tooth 52 and 52a has a substantially vertical wall 54 and a sloped wall 56. Teeth 52 are positioned to engage ribs 40 during attachment of adapter 14 to syringe 12 as will be discussed in further detail below. Top and bottom walls 50 include a pair of inwardly extending walls 50a which define an external concavity 58 which juts radially inwardly towards coupling member 34. A projection or tab 60 extends from each of top and bottom walls 50 from within each respective concavity 58 radially outwardly beyond the outermost extent of top and bottom walls 50. Collar portion 32 is secured to body portion 30 of adapter 14 by diametrically opposed spring members 53 which extend between body portion 30 and sidewalls 48 of collar portion 32. Spring members 53 urge sidewalls inwardly such that teeth 52 on sidewalls 48 engage ribs 40, but are flexible to allow sidewalls 48 to flex outwardly to allow teeth 52 to ratchet over ribs 40 during attachment of adapter 14 to syringe 12.

In order to attach oral dose tip adapter 14 to a syringe 12, coupling member 34 is inserted into an annular recess 70 (FIG. 2) defined between coupling member 28 and fluid outlet 26 and rotated in relation to coupling member 28 in a first direction (clockwise) such that tabs 34a of coupling member 34 engage and interlock with threads 28a of coupling member 28. As oral dose tip adapter 14 is rotated in relation to syringe 12, teeth 52 of collar portion 32 engage ribs 40 of coupling member 28. Teeth 52 and ribs 40 are positioned such that during attachment of tip adapter 14 to syringe 12, sloped sidewalls 44 of ribs 40 engage sloped walls 56 of teeth 52. Engagement of sloped sidewalls 44 and sloped walls 56 causes sidewalls 48 of collar portion 32 to be cammed or flexed outwardly to allow teeth 52 to pass or ratchet over ribs 40 to facilitate rotatable attachment of coupling member 34 of tip adapter 14 to coupling member 28 of syringe 12. It is noted that teeth 52a may be positioned to engage ribs 40 during attachment of adapter 14 to syringe 12 or alternatively, teeth 52a may be positioned to engage ribs 52a only when tabs 60 are pressed together as will be discussed in further detail below. When attached, fluid outlet 26 is positioned within fluid channel 36 of body portion 30 of adapter 14 to fluidly couple syringe 12 to adapter 14.

In the event a clinician attempts to remove tip adapter 14 from syringe 12 by rotating tip adapter 14 in relation to syringe 12 in a second direction (counter-clockwise), substantially vertical sidewalls 42 of ribs 40 engage substantially vertical walls 54 of teeth 52 to prevent relative rotation of coupling member 34 of tip adapter 14 with respect to coupling member 28 of syringe 12 and, thus, prevent separation of tip adapter 14 from syringe 12. As discussed above, spring members 53 urge teeth 52 on sidewalls 48 into engagement with ribs 40 on coupling member 48.

In use, after oral dose tip adapter 14 has been attached to a syringe 12, tip portion 30 of oral dose tip adapter 14 is positioned within a patient's mouth and syringe 12 is actuated to inject fluid from reservoir 18 of syringe 12 into a patient's mouth. In some instances, the patient is an infant or small child who may be teething or combative and bite down on the tip adapter 14 or collar portion 32 of the tip adapter 14 during oral dosing. In order to minimize the likelihood that such biting action will disengage teeth 52 from ribs 40 and possibly disengage tip adapter 14 from syringe 12 within an infant's or small child's mouth, collar portion 32 has been uniquely designed. More specifically, as described above, collar portion 32 has a substantially elliptical or oval cross-section with teeth 52 formed along an inner surface of sidewalls 48 of collar portion 32 and teeth 52a formed on an inner surface of top and bottom walls 50. If an infant or child were to bite down on sidewalls 48 of collar portion 32, teeth 52 of collar portion 32 would be pressed into engagement with ribs 40 to prevent rotation of coupling member 34 in relation to coupling member 28 and minimize the likelihood of disengagement of tip adapter 14 from syringe 12. If an infant or small child were to bite down on top and bottom walls 50 of collar portion, the infant or small child would compress tabs or protrusions 60 inwardly to urge teeth 52a into engagement with ribs 40 to prevent rotation of coupling member 34 in relation to coupling member 28 and minimize the likelihood of disengagement of tip adapter 14 from syringe 12. Because infants and small children may swallow and choke or asphyxiate on a disengaged tip adapter 14, the configuration of collar portion 32 provides valuable benefits to the assembly described above.

Figure 9:
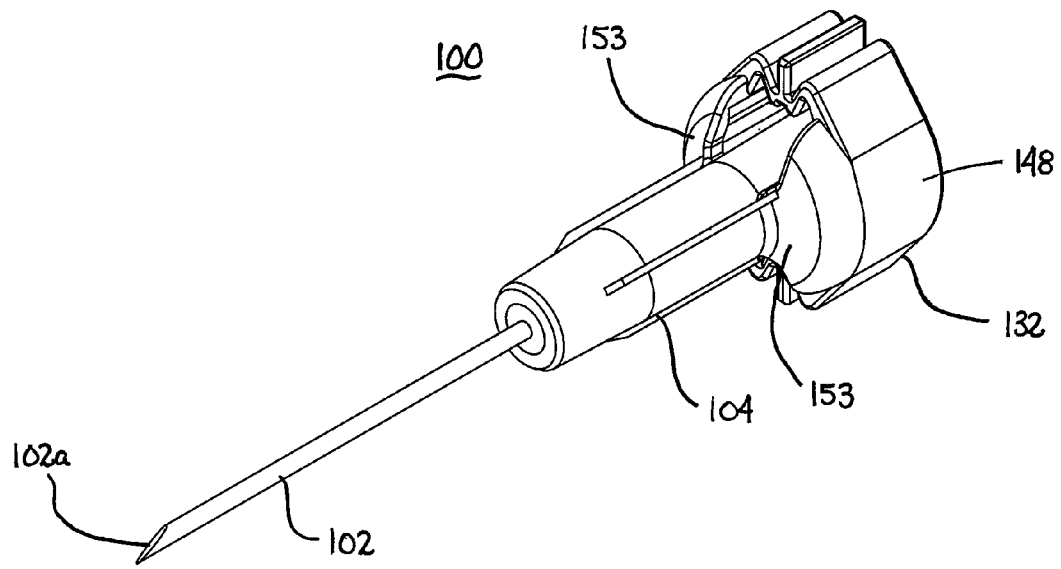
FIG. 9 is a side perspective view of one embodiment of a needle hub assembly adapter in accordance with the principles of the present disclosure.
Figure 10:
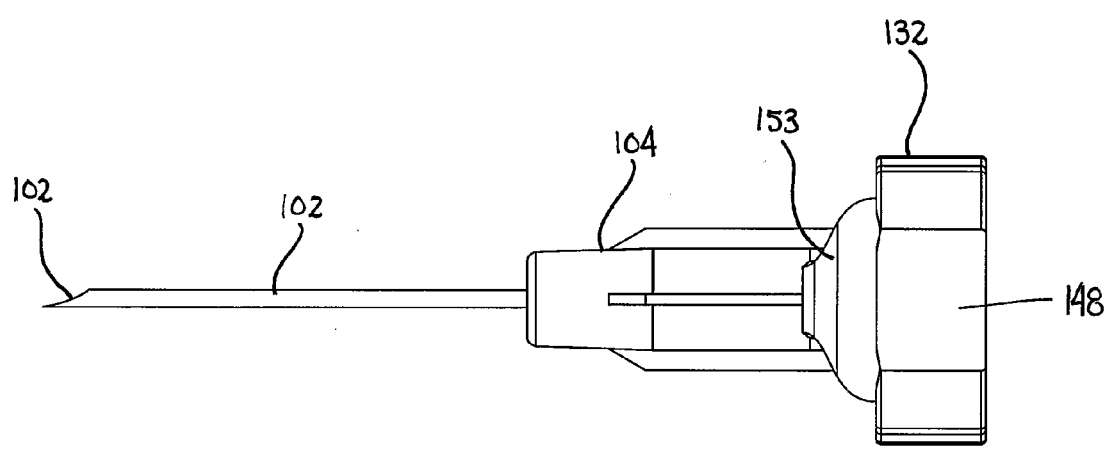
FIG. 10 is a side view of the needle hub assembly adapter shown in FIG. 9.

Referring to FIGS. 9 and 10, the presently disclosed anti-rotation, removal resistant adapter and collar portion may also be incorporated into a needle hub assembly shown generally as 100. Needle hub assembly 100 includes a needle cannula 102 having a sharpened distal end 102a and a needle hub 104. Needle cannula 102 is hollow and defines a fluid passageway and can be secured to needle hub 104 using any known fastening technique, e.g., adhesives, crimping, welding, etc. Collar portion 132, which is substantially identical to collar portion 32 described above, is secured to needle hub 104 by spring members 153 which extend between collar portion 132 and needle hub 104. Spring members 153 function in an identical fashion to spring members 53 and urge sidewalls 148 of collar portion 132 inwardly. Needle hub 104 also includes a male luer-type coupling member (not shown) which is substantially similar to luer connector 34 (FIG. 3) described above to facilitate connection of needle hub assembly 100 to a syringe 12 (FIG. 1) as described above.

As discussed above, collar portion 132 of needle hub assembly 100 provides an anti-rotation, removal resistant structure to prevent separation of needle hub assembly 100 and syringe 12 after needle hub assembly 100 has been attached to syringe 12. This feature is particularly important in needle hub assemblies which are used with syringes which have high injection pressures. More specifically, the pressurized fluid which is ejected from a syringe through a needle hub assembly applies a pressure on the needle hub assembly which tends to push the needlehub assembly away from the syringe and separate the needle hub assembly from the syringe. Depending on the torque used to secure the needle hub assembly to the syringe, higher pressure syringes may effect this result. The presently disclosed needle hub assembly 100 with the anti-rotation, removal resistant adapter reduces the likelihood that the needle hub assembly will separate from a syringe at any given fluid injection pressure. It is also noted that the presently disclosed adapter, because of the increase in purchase between the adapter and the syringe coupling, enables a doctor to torque down further on the needle hub when the needle hub is secured to a syringe.

Referring again to FIG. 3, in alternative embodiment of oral dose tip adapter 14 and needle hub assembly 100 not shown, teeth 52 and 52a are formed only on the distal portion of the inner surface of the collar portion. Thus, when tip adapter 14 or needle hub assembly 100 is attached to a syringe 12, teeth 52 and 52a will not engage ribs 40 until adapter 14 and needle hub assembly 100 are in partial rotatable engagement with syringe 12. The positioning of teeth 52 and 52a on the inner surface of the collar portion can be selected such that teeth 52 and 52a engage ribs 40 at any point during rotatable engagement of hub assembly 100 and/or oral dose tip adapter 14 with syringe 12. It is noted that the further teeth 52 and 52a are moved distally from the proximal end of the collar portion, the more fully rotatably engaged the collar portion and the syringe will be before the teeth engage the ribs. Moving the location of the teeth distally within the collar portion reduces the force required to attach the oral dose tip and the needle hub assembly to the syringe but reduces the resistance to detachment. Thus, the position of the teeth on the inner surface of the collar portion should be selected based upon the intended use of the device. For example, if the collar portion is to be used on a hub assembly for delivering high pressure fluids, the teeth may be positioned further proximally on the collar portion than if the collar portion is to be used on a hub assembly for delivering low pressure fluids.

It will be understood that various modifications may be made to the embodiments disclosed herein. For example, the coupling members described herein may be selected from a wide variety of known coupling members. Further, the exact configuration of the collar portion and/or the teeth and rib ratcheting structure may be varied so long as the structure allows for attachment of the adapter tip to a syringe while resisting detachment. Therefore, the above description should not be construed as limiting, but merely as exemplifications of preferred embodiments. Those skilled in the art will envision other modifications within the scope and spirit of the claims appended hereto.

What is claimed is:

1. An adapter and syringe assembly comprising:
a syringe having a body defining a fluid reservoir, a plunger assembly including a plunger head dimensioned to be slidably received within the reservoir, a fluid outlet, and a first coupling member; and
an adapter including a body portion defining a fluid channel, an oval collar portion, and a second coupling member configured to engage the first coupling member to secure the adapter to the syringe;
wherein the syringe includes at lease one rib and a surface of the collar portion includes at least one protrusion, the at least one rib and the at least one protrusion being configured and positioned to interact to facilitate attachment of the adapter to the syringe but to resist detachment of the adapter from the syringe.

2. The assembly according to claim 1, wherein the body portion of the adapter defines an oral dose tip.

3. The assembly according to claim 1, wherein the first coupling member and the second coupling member are configured to be rotatably coupled.

4. The assembly according to claim 3, wherein the first coupling member is substantially annular.

5. The assembly according to claim 4, wherein the at least one rib is formed on an external surface of the first coupling member.

6. The assembly according to claim 5, wherein the at least one protrusion is formed on an inner surface of the collar portion, the at least one protrusion being positioned to engage the at least one rib to resist rotatable detachment of the adapter from the syringe.

7. The assembly according to claim 6, further including at least one spring member connecting the collar portion to the body portion, the at least one spring member urging the at least one protrusion into engagement with the at least one rib.

8. The assembly according to claim 6, wherein the at least one protrusion includes a plurality of protrusions and the at least one rib includes a plurality of ribs.

9. The assembly according to claim 8, wherein the plurality of ribs are spaced about the first coupling member and the plurality of protrusions are positioned about the inner surface of the collar portion.

10. The assembly according to claim 9, wherein the collar portion includes a pair of sidewalls, a top wall and a bottom wall.

11. The assembly according to claim 10, wherein the plurality of protrusions are positioned on the inner surface of the pair of sidewalls of the collar portion and on an inner surface of the top and bottom walls.

12. The assembly according to claim 11, wherein the top and bottom walls of the collar portion define an external concavity.

13. The assembly according to claim 12, wherein the collar portion further includes a first tab extending within the concavity from the top wall of the collar portion and a second tab extending within the concavity from the bottom wall of the collar portion, the top and bottom walls being configured such that when the first and second tabs are compressed towards each other, the protrusions of the top and bottom walls securely engage the ribs on the first coupling member.

14. The assembly according to claim 13, wherein the first and second tabs extend outwardly of a periphery of the collar portion.

15. The assembly according to claim 1, wherein the first and second coupling members are leur-type connectors.

16. The assembly according to claim 1, wherein the body portion, the collar portion and the second coupling member are integrally formed.

17. The assembly according to claim 1, wherein the at least one rib and the at least one protrusion include a plurality of ribs and a plurality of protrusions.

18. The assembly according to claim 17, wherein the plurality of ribs are formed on the first coupling member and the plurality of protrusions are positioned on an inner surface of the collar portion, the first and second coupling members being configured for rotatable engagement such that the plurality of protrusions ratchet over the plurality of ribs during rotatable attachment of the first and second coupling members.

19. The assembly according to claim 18, wherein the plurality of ribs and the plurality of protrusions are configured to resist detachment of the first coupling member from the second coupling member.

20. An adapter and syringe assembly comprising:
a syringe having a body defining a fluid reservoir, a plunger assembly including a plunger head dimensioned to be slidably received within the reservoir, a fluid outlet, and a first coupling member; and
an adapter including a body portion defining a fluid channel, a collar portion, and a second coupling member configured to engage the first coupling member to secure the adapter to the syringe, the body portion defining an oral dose tip;
wherein the syringe includes a plurality of ribs spaced about the first coupling member and the adapter includes a plurality of protrusions positioned about the inner surface of the collar portion, the plurality of ribs and the plurality of protrusions being configured and positioned to interact to facilitate rotatable attachment of the adapter to the syringe but to resist rotatable detachment of the adapter from the syringe and wherein the collar portion is substantially oval and includes a pair of sidewalls and top and bottom walls, the plurality of protrusions being positioned on an inner surface of the pair of sidewalls and on an inner surface of the top and bottom walls.

21. The assembly according to claim 20, wherein the top and bottom walls of the collar portion define an external concavity.

22. The assembly according to claim 21, wherein the collar portion further includes a first tab extending within the concavity from the top wall of the collar portion and a second tab extending within the concavity from the bottom wall of the collar portion, the top and bottom walls being configured such that when the first and second tabs are compressed towards each other, the protrusions on the top and bottom walls securely engage the ribs on the first coupling member.

23. An adapter and syringe assembly comprising:
a syringe having a body defining a fluid reservoir, a plunger assembly including a plunger head dimensioned to be slidably received within the reservoir, a fluid outlet, and a first coupling member; and
wherein the syringe includes a plurality of ribs spaced about the first coupling member and the adapter includes a plurality of protrusions positioned about the inner surface of the collar portion, the plurality of ribs and the plurality of protrusions being configured and positioned to interact to facilitate rotatable attachment of the adapter to the syringe but to resist rotatable detachment of the adapter from the syringe and wherein the collar portion is substantially oval and includes a pair of sidewalls and top and bottom walls, the plurality of protrusions being positioned on an inner surface of the pair of sidewalls and on an inner surface of the top and bottom walls.

24. The assembly according to claim 23, wherein the top and bottom walls of the collar portion define an external concavity.

25. The assembly according to claim 24, wherein the collar portion further includes a first tab extending within the concavity from the top wall of the collar portion and a second tab extending within the concavity from the bottom wall of the collar portion, the top and bottom walls being configured such that when the first and second tabs are compressed towards each other, the protrusions on the top and bottom walls securely engage the ribs on the first coupling member.

* * * * *